(12) United States Patent
Northern

(10) Patent No.: US 10,073,059 B2
(45) Date of Patent: Sep. 11, 2018

(54) APPARATUS AND METHOD FOR DETECTING DEFECTS IN A METALLIC SURFACE BY MOVING AN EDDY COIL ALONG A SCAN PATH RELATIVE TO THE SURFACE

(75) Inventor: Robert Northern, Derbyshire (GB)

(73) Assignee: SARCLAD LIMITED, Rotherham (GB)

( * ) Notice: Subject to any disclaimer, the term of this patent is extended or adjusted under 35 U.S.C. 154(b) by 403 days.

(21) Appl. No.: 14/128,386

(22) PCT Filed: Jun. 12, 2012

(86) PCT No.: PCT/GB2012/000504
§ 371 (c)(1),
(2), (4) Date: Jun. 9, 2014

(87) PCT Pub. No.: WO2012/175909
PCT Pub. Date: Dec. 27, 2012

(65) Prior Publication Data
US 2014/0292316 A1 Oct. 2, 2014

(30) Foreign Application Priority Data
Jun. 23, 2011 (GB) .................................. 1110678.8

(51) Int. Cl.
*G01N 27/90* (2006.01)
(52) U.S. Cl.
CPC ....... *G01N 27/9073* (2013.01); *G01N 27/902* (2013.01); *G01N 27/908* (2013.01)
(58) Field of Classification Search
CPC . G01N 27/908; G01N 27/902; G01N 27/9073
(Continued)

(56) References Cited

U.S. PATENT DOCUMENTS

| 4,876,506 A | * | 10/1989 | Brown | .................. G01B 7/281 324/207.12 |
| 7,272,254 B2 | | 9/2007 | Shankarappa et al. | |

(Continued)

FOREIGN PATENT DOCUMENTS

| CN | 1576829 A | 2/2005 |
| EP | 0165051 A2 | 12/1985 |

(Continued)

OTHER PUBLICATIONS

Great Britain Search Report dated Sep. 14, 2012 for Great Britain Patent Application No. 1210420.4.
(Continued)

*Primary Examiner* — Jay Patidar
(74) *Attorney, Agent, or Firm* — David D. Brush; Westman, Champlin & Koehler, P.A.

(57) ABSTRACT

An apparatus and method detect defects in a metal surface. The apparatus is configured to move an eddy coil relative to an underlying metallic surface along a plurality of generally parallel and adjacent scan paths, and to receive from the eddy coil an oscillating signal induced at said coil as it is moved along each path. A representation of the received oscillating signal in relation to each one of a plurality of adjacent scan areas within each path is recorded, and a two-dimensional grid-like map showing the signal representations relative to each scan area is displayed. Defect location is facilitated by a further function of the apparatus and method, by which user input to an interface causes a light source to illuminate a selected part of the metallic surface.

25 Claims, 8 Drawing Sheets

(58) Field of Classification Search
USPC .................................................. 324/219–222
See application file for complete search history.

(56) References Cited

U.S. PATENT DOCUMENTS

2005/0008213 A1* 1/2005 Shankarappa ........... G06K 9/00
                                                          382/141
2009/0033323 A1    2/2009 Georgeson et al.

FOREIGN PATENT DOCUMENTS

| EP | 0219477 A1   | 4/1987  |
|----|--------------|---------|
| EP | 0533440 A1   | 3/1993  |
| EP | 1710571 A1   | 10/2006 |
| EP | 1801575 A1   | 6/2007  |
| EP | 1808693 A1   | 7/2007  |
| EP | 1939616 A1   | 7/2008  |
| GB | 1513192 A    | 6/1978  |
| GB | 2124772 A    | 2/1984  |
| WO | 02/50523 A2  | 6/2002  |
| WO | 2009083674 A1 | 7/2009 |
| WO | 2010015806 A1 | 2/2010 |

OTHER PUBLICATIONS

J.E.S. Macleod: "Pattern Classification in the Automatic Inspection of Tubes Scanned by a Rotating Eddy-Current Probe", Department of Electronics and Electrical Engineering, University of Glasgow, Glasgow G12 8QQ, Scotland, 1982 IEEE, XP001331847, 3 pages.
International Search Report and Written Opinion dated Oct. 1, 2012 for corresponding International Application No. PCT/GB2012/000504, filed Jun. 12, 2012.
English translation of the Chinese Office Action dated Apr. 5, 2016 for corresponding Chinese Application No. 201280041275.9.
Macleod et al., "Automatic inspection of tubes scanned by a rotating eddy-current probe", Signal Processing 5, pp. 145-450, Jan. 31, 1983.

* cited by examiner

APPARATUS AND METHOD FOR DETECTING DEFECTS IN A METALLIC SURFACE BY MOVING AN EDDY COIL ALONG A SCAN PATH RELATIVE TO THE SURFACE

CROSS-REFERENCE TO RELATED APPLICATIONS

This Application is a Section 371 National Stage Application of International Application No. PCT/GB2012/000504, filed Jun. 12, 2012, which is incorporated by reference in its entirety and published as WO 2012/175909 on Dec. 27, 2012, in English.

FIELD OF THE DISCLOSURE

The present invention relates to an apparatus and method for detecting defects in a metallic surface. Particularly, though not exclusively, the invention relates to a method of detecting defects in hot and cold mill rolls.

Methods and apparatus for detecting longitudinal defects in mill rolls using eddy current inspection machines are known. One such method and apparatus is disclosed in the Applicant's earlier international patent no. WO2010/015806.

The Applicant has sought to improve the aforementioned defect detection method and apparatus and, in doing so, has developed a method and apparatus suitable for detecting circumferential defects on a mill roll as well as longitudinal defects. The method and apparatus developed also allows the location of defect, once detected, to be easily and precisely located.

BACKGROUND OF THE DISCLOSURE

The use of non-contact eddy current coil technology is known for use in detecting defects in such products. The product under test passes through or adjacent to an electrical test coil which has been excited by an alternating current. This induces a flow of eddy currents around the test material, or, in the case of a sector coil, in the area under the coil. Short, intermittent anomalies or flaws cause a variation in the eddy current pattern which the instrument detects.

The minimum flaw length which can be consistently detected is a function of the size of the coil employed and throughput speed of the mill roll and its rotary speed.

Such detection equipment can be mounted onto roll grinding equipment, before, during and after roll grinding activities to effectively detect and quantify surface defects such as roll cracks, bruising and magnetism The coil oscillation frequency is, put simply, measured, de-modulated to extract defect information from the carrier wave, ac de-coupled and amplified to produce a signal from which the defect can be recognized.

The very nature of defect detection is to detect changes in sensed signals. Consequently, de-modulation has always been critical to enable the extraction of the defect signal from the carrier. Following demodulation filtering has always been used to remove any background noise and changes in frequency caused solely by slight contours in the mill roll. This de-modulation and filtering process requires prior knowledge of the mill roll's diameter in order to work correctly The Applicant has recognized that this de-modulation of the frequency causes, in many cases, circumferential defects to go undetected as the frequency remains constant across the defect thereby causing the instrument to record only a minute change in frequency at the start of the defect and a further minute change in frequency at the end of the defect. To even the trained eye, the changes appear to be two small (longitudinal) defects, which are hard to see and may even be missed altogether.

Moreover, as known systems of detection are dependent on the rotational and through-speed of the mill roll, precise location of any defect, once detected, is cumbersome and time consuming.

SUMMARY

The present invention seeks to alleviate the aforementioned disadvantages with known detection apparatuses and methods by providing an improved apparatus and method, for example one which can detect circumferential defects on a mill roll and provide a means of locating detected defects easily and efficiently.

According to an aspect of the invention, there is provided an apparatus for detecting defects in a metallic surface, comprising: a receiver for receiving from an eddy coil an oscillating signal induced at the eddy coil as it is moved along a scan path between first and second positions relative to an underlying metallic surface; recording means for recording the oscillating signal received along the scan path between the first and second positions; and output means for outputting to a display a representation of the recorded oscillating signal for the scan path.

The recorded oscillating signal in this context is the received signal from the eddy coil which has not undergone demodulation, or similar processing, to extract defect information from a carrier wave. Thus, the representation of the recorded oscillating signal is based on the non-demodulated signal received from the eddy coil.

According to a further aspect, there is provided apparatus for detecting defects in a metal surface, the apparatus comprising: an eddy coil movable relative to an underlying metallic surface over a plurality of orthogonally arranged scan areas; a receiver for receiving from the eddy coil the oscillating signal induced at said coil as it is moved over each scan area; signal processing means for: generating a representation of the received oscillating signal in relation to each scan area, and generating a two-dimensional grid-like map showing the signal representations in relation to each scan area; and means for outputting the grid-like map to a display.

According to a further aspect, there is provided a method of detecting defects in a metallic surface, the method comprising: receiving from an eddy coil an oscillating signal induced at the eddy coil as it is moved along a scan path between first and second positions relative to an underlying metallic surface; recording the oscillating signal received along the scan path between the first and second positions; and outputting to a display a representation of the oscillating signal for the scan path.

According to a further aspect, there is provided a method for detecting defects in a metal surface, the method comprising: moving an eddy coil relative to an underlying metallic surface along a plurality of generally parallel and adjacent scan paths; receiving from the eddy coil an oscillating signal induced at said coil as it is moved along each path; generating a representation of the received oscillating signal in relation to each one of a plurality of adjacent scan areas within each path; generating a two-dimensional grid-like map showing the signal representations relative to each scan area; and means for outputting the grid-like map to a display.

According to a further aspect of the invention, there is provided a method of detecting defects in a metallic surface including the steps of:
(a) passing an eddy coil circuit over the metallic surface;
(b) recording the raw oscillation data received for the length of the surface under test; and
(c) outputting a representation of the raw oscillation data for display purposes.

By "raw data" it is meant the un-processed data from the eddy coils and ultrasonic coils that has not undergone de-modulation.

Preferably the metallic surface comprises a substantially cylindrical product. The product will preferably take the form of a steel mill roll.

Preferably the measurements are recorded over a coil frequency of approximately 180 kHz. This is substantially lower than known techniques.

According to a further aspect of the invention, there is provided a method of detecting and locating defects in a metallic surface including the steps of:
(a) passing a test head incorporating an eddy coil circuit over the metallic surface;
(d) recording the raw oscillation data received for the length of the surface under test;
(e) outputting a representation of the raw data on a screen display;
(b) displaying the location of the test head on the screen display;
(c) reviewing the screen display to identify potential defects; and
(d) moving the metallic surface with respect to the test head, and/or moving the test head with respect to the metallic surface, to a position where the displayed location of the test head and the defect area overlap on the screen display.

Preferably the screen display is a touch screen wherein the defect area can be touched to allow automated movement of the test head and/or metallic surface to the position of overlap.

Preferably the test head includes a light emitting means which is activated at the point of overlap to emit a light on to the metallic surface over the defect location.

According to a further aspect of the invention, there is provided a computer program comprising instructions that when executed by computer apparatus control it to perform the method aforementioned.

According to a further aspect of the invention, there is provided a non-transitory computer-readable storage medium having stored thereon computer-readable code, which, when executed by computing apparatus, causes the computing apparatus to perform a method comprising:
(a) passing an eddy coil circuit over the metallic surface;
(b) recording the raw oscillation data received for the length of the surface under test; and
(c) outputting a representation of the raw oscillation data for display purposes.

According to a further aspect of the invention, there is provided a non-transitory computer-readable storage medium having stored thereon computer-readable code, which, when executed by computing apparatus, causes the computing apparatus to perform a method comprising:
(a) passing a test head incorporating an eddy coil circuit over the metallic surface;
(b) recording the raw oscillation data received for the length of the surface under test;
(c) outputting a representation of the raw data on a screen display;
(d) displaying the location of the test head on the screen display;
(e) reviewing the screen display to identify potential defects; and
(f) moving the metallic surface with respect to the test head, and/or moving the test head with respect to the metallic surface, to a position where the displayed location of the test head and the defect area overlap on the screen display.

According to a further aspect of the invention, there is provided apparatus, the apparatus having at least one processor and at least one memory having computer-readable code stored thereon which when executed controls the at least one processor:
(a) passes an eddy coil circuit over the metallic surface;
(b) records the raw oscillation data received for the length of the surface under test; and
(c) outputs a representation of the raw oscillation data for display purposes.

According to a further aspect of the invention, there is provided apparatus, the apparatus having at least one processor and at least one memory having computer-readable code stored thereon which when executed controls the at least one processor:
(a) passes a test head incorporating an eddy coil circuit over the metallic surface;
(b) records the raw oscillation data received for the length of the surface under test;
(c) outputs a representation of the raw data on a screen display;
(d) displays the location of the test head on the screen display;
(e) reviews the screen display to identify potential defects; and
(f) moves the metallic surface with respect to the test head, and/or moving the test head with respect to the metallic surface, to a position where the displayed location of the test head and the defect area overlap on the screen display.

BRIEF DESCRIPTION OF THE DRAWINGS

Embodiments of the invention will now be described by way of the example with reference to the accompanying Figures in which.

DETAILED DESCRIPTION OF ILLUSTRATIVE EMBODIMENTS

Figure 1:
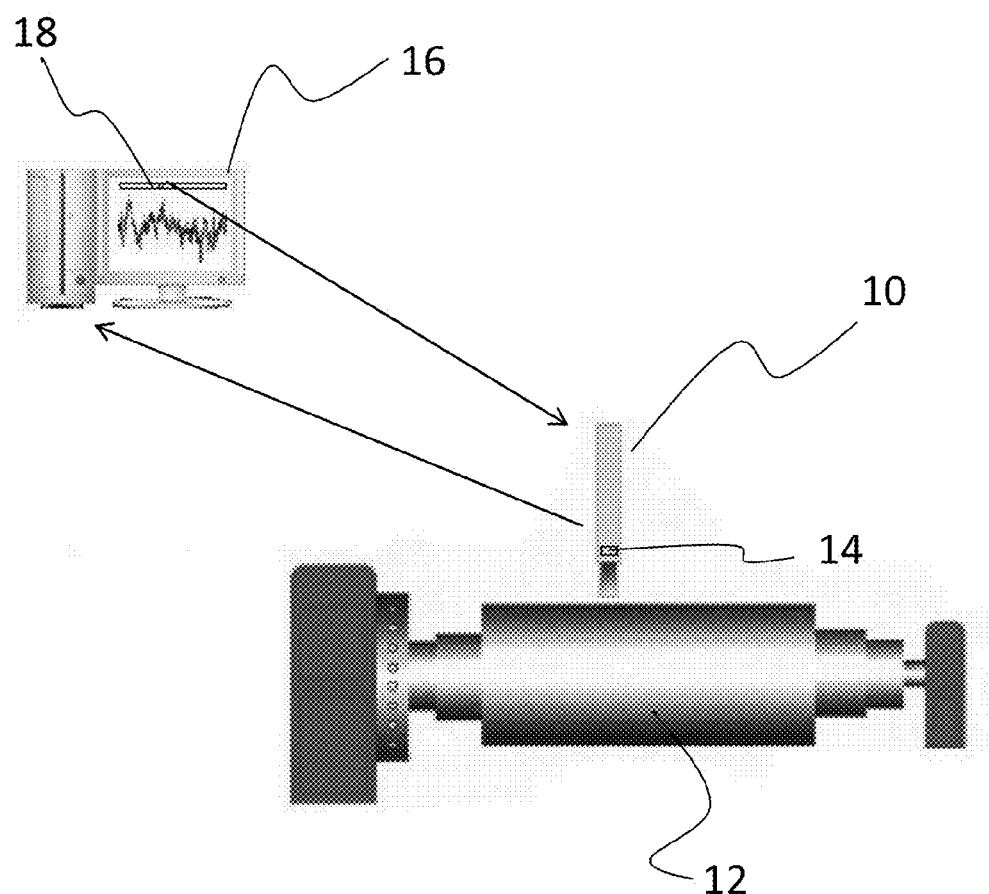
FIG. 1 illustrates an apparatus arranged in accordance with a first embodiment the invention.

Referring to FIG. 1, a first embodiment comprises a test head 10 incorporating non-contact eddy current and ultrasonic coils. The test head 10 is designed to be mounted onto a roll grinding machine such that the test head 10 is slidable longitudinally adjacent to a steel mill roll 12 which is, in use, on the grinding machine.

The test head 10 includes an LED 14 which, during use, is activated to emit light onto a section of the mill roll 12 surface, as will be later described.

During use, the test head 10 is moved across the length of the mill roll 12 whilst at the same time the mill roll 12 rotates on the grinding machine.

The oscillation frequency of the eddy coils within the test head 10 is continually measured and recorded across the entire length of the coil. The raw data is then transmitted to a processing means for display on a touch screen 16.

From the display of raw data, a user is able to clearly see changes in the wave frequency across the mill roll 12. The fact that the data recorded is raw and not de-modulated means that the entire wave pattern is displayed thereby showing clearly areas of constant waves at a higher frequency indicative of a circumferential defect in the mill roll.

Figures 2A, 2B:
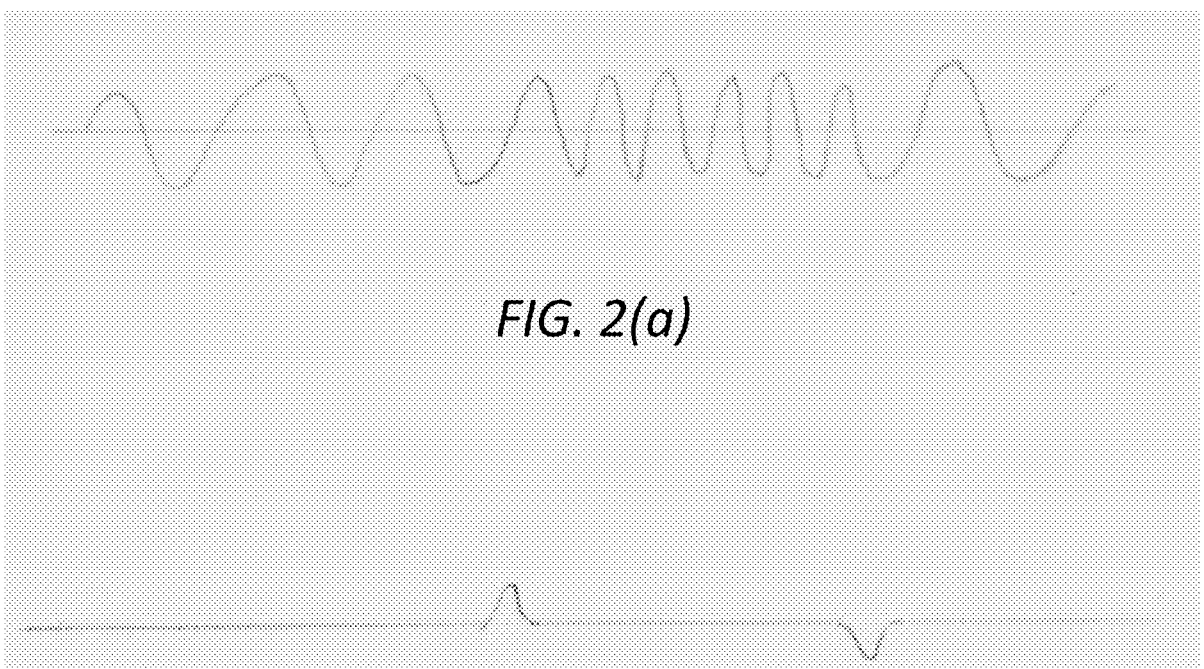
FIGS. 2(a) and 2(b) illustrate displays of un-modulated and demodulated frequency wave data.

FIGS. 2(a) and 2(b) illustrate schematically a basic display of wave frequency over a circumferential defect. The difference between the two displays is that the display of FIG. 2(a) is that of the present embodiment, whereby the raw frequency data is displayed and the display of FIG. 2(b) is that of a frequency or phase de-modulated frequency signal which is standard practice in the industry.

It is clear from the comparison of FIGS. 2(a) and (b) that a circumferential defect is clearly indicated in 2(a) whereas 2(b) may also indicate two separate longitudinal defects.

Data concerning the relative position of the test head 10 to the mill roll 12 is also transmitted to the processing means and the touch screen 16 for display above the frequency waves. The location of the test head 10 may be displayed in such a basic form as a vertical line 18.

During use, once the mill roll has been "scanned" by the test head 10 and the wave frequency across the entire mill roll 12 is displayed on the touch screen 16, a user can simply identify a defect area, whether it be a longitudinal or circumferential defect and touch the screen 16 at the area to highlight it.

The test head 10 can be moved manually or automatically with respect to the mill roll 12, to the correct location by lining up the display indicator 18 on the touch screen 16 with the highlighted area of the frequency wave.

The mill roll 12 may also be manually or automatically rotated for the correct orientation.

When the test head 10 is located over the position highlighted, the LED 14 located on the test head 10 activates to emit a light over the defect area of the mill roll 12. The LED may flash on and off as the test head 10 approaches the correct position to further aid the user, the flashing becoming faster as the test head moves towards said correct position. The correct position may be indicated by a non-flashing LED or a change in LED colour.

The fact that the entire frequency wave is measured and the raw data used for processing detection and location of defects on or within the surface of the mill roll means that the measurements are not dependent on the through-speed or the rotational speed of the mill roll 12. Indeed, the mill roll 12 may be manually or automatically moved back and forth and rotated several times to find achieve the correct location of the defect.

A second embodiment will now be described with reference to FIGS. 3 to 10.

Figure 3:
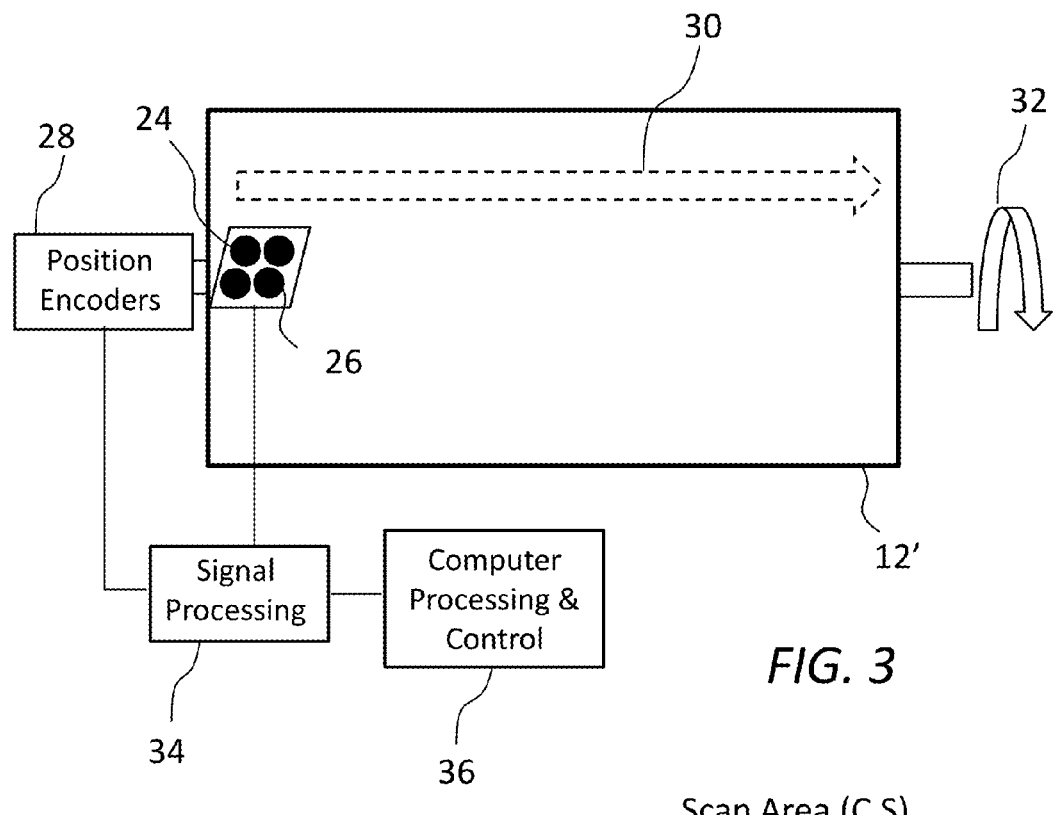
FIG. 3 illustrates an apparatus in accordance with a second embodiment of the invention.

Referring to FIG. 3, there is shown a steel mill roll 12' mounted on a grinding machine. A defect detection system according to the second embodiment comprises a test head 24 on which are mounted four eddy current coils 26, although fewer or a greater numbers of coils can be used (the concept is scalable in that sense). As with the first embodiment, the test head 24 is capable of being mounted onto a roll grinding machine such that the test head is movable longitudinally adjacent to the steel mill roll 12', as indicated by the arrow 30.

Arrow 32 indicates the rotational movement of the mill roll 12' on the grinding machine.

The test head 24 and therefore each eddy coil 26 are movable along a plurality of adjacent, longitudinal scan paths.

The defect detection system in this second embodiment also comprises position encoders 28 which provide data indicative of the rotational position of the mill roll 12' and the longitudinal position of the test head 24. Where position encoders are provided in-situ on the roll grinding machine, the system can simply take data from said in-situ position encoders.

As will be explained below with reference to FIG. 4, the system is configured such that each coil 26 scans a plurality of orthogonally-arranged 'scan areas' on the mill roll surface. Data received from the position encoders 28 is used to identify in real-time which scan area a particular coil 26 is located over.

The defect detection system also comprises a signal processing module 34 and a computer processing and control module 36, the latter of which includes a touch-screen display means and a defect locator means.

Figure 4:
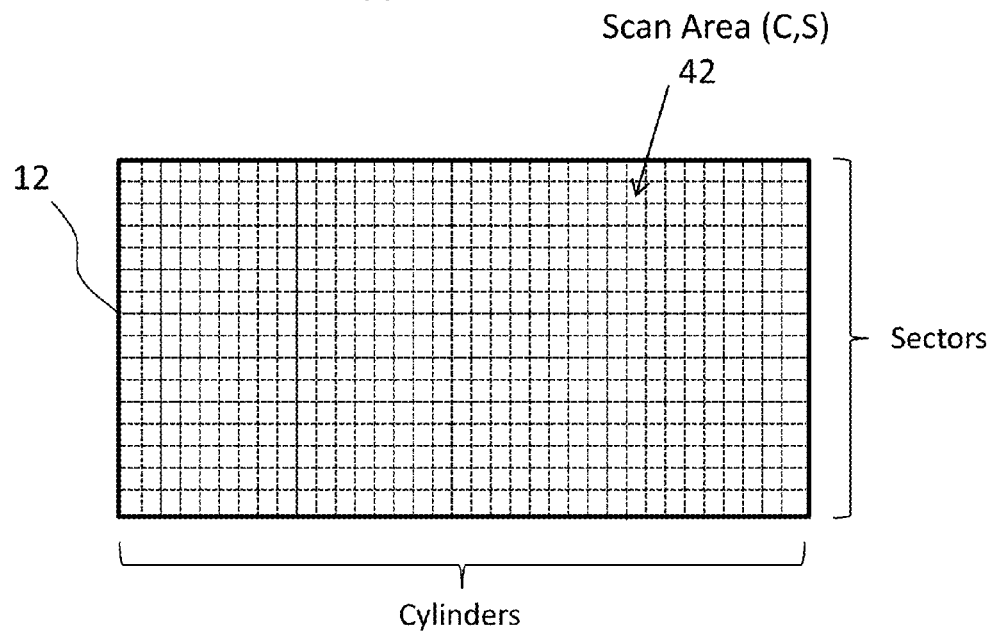
FIG. 4 is a schematic view of a scan map generated using the apparatus of FIG. 3, the map representing the surface of a mill roll.

Referring now to FIG. 4, software within the computer processing and control module 36 effectively maps the entire mill roll surface as a plurality of orthogonally arranged squares or rectangles 42, each of which provides a particular scan area for testing. Each scan area is uniquely referenced by a cylinder number (C) and a sector number (S); in this regard, the length of the mill roll surface is divided into an integer number of cylinders and the circumferential surface into an integer number of sectors. The computer processing and control module 36 is configured to identify which scan area a particular coil 26 is located over at any one time based on data received from the position encoders 28.

Figure 5:
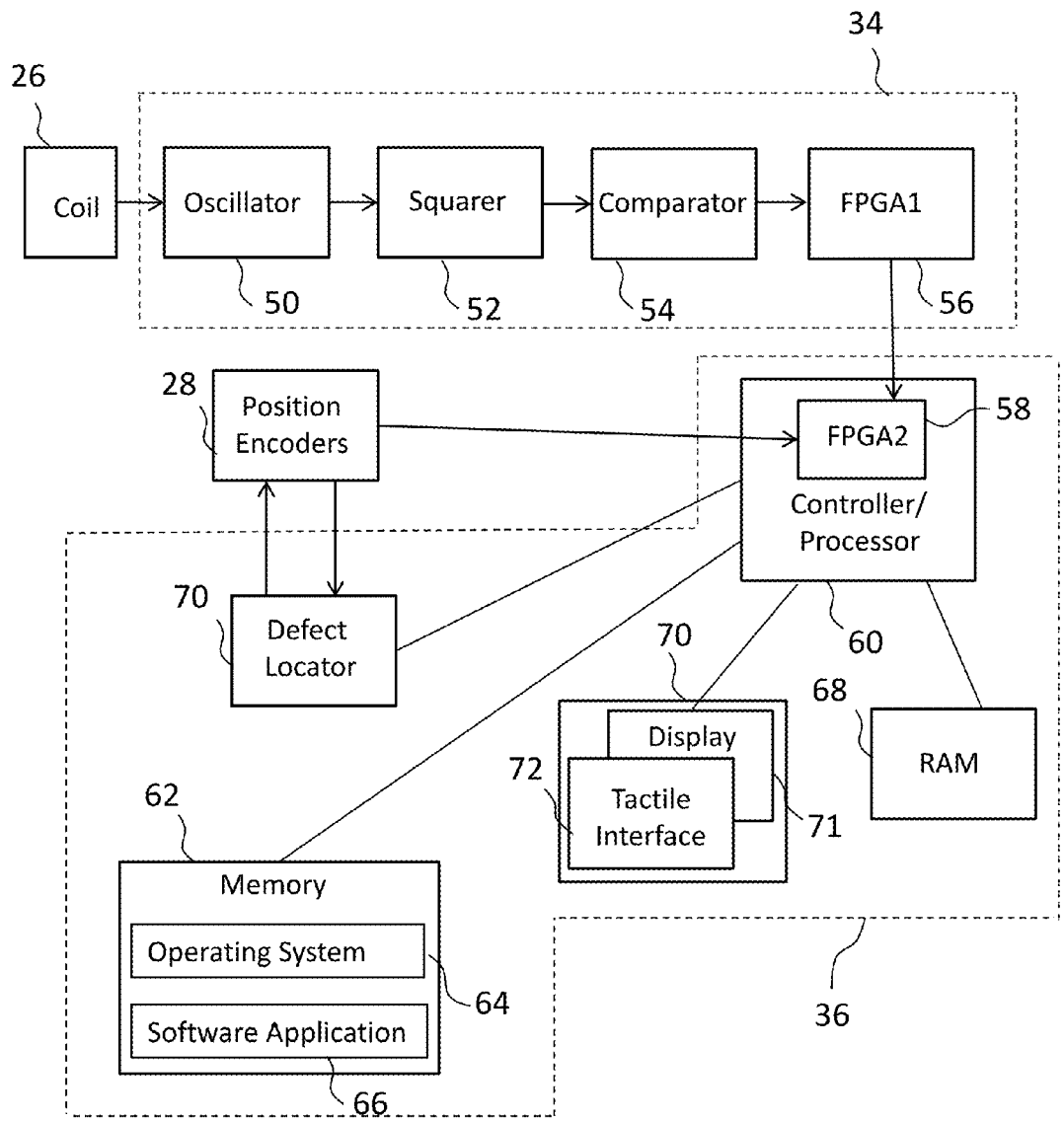
FIG. 5 is a block diagram showing components of a signal processing module and a computer processing and control module forming part of the apparatus of FIG. 3.

Referring now to FIG. 5, there is shown a schematic diagram of components of the signal processing module 34 and the computer processing and control module 36. For ease of explanation, the operation of each component will be described in relation to a single coil 26.

The signal processing module 34 takes as input the raw oscillation signal generated by the coil 26, driven by an oscillator 50 e.g. as shown in FIG. 2(a). This signal is fed into a squarer 52 and comparator 54. The output from the comparator 54 is a square wave, having the exact frequency of the raw oscillation signal from the coil.

It will therefore be appreciated that the raw signal is utilised rather than a frequency or phase demodulated version.

The comparator output signal is fed to a Field Programmable Gate Array (FPGA) 56 which is configured to measure the time taken for a predetermined number of oscillations to occur. This predetermined number is, in theory arbitrary, though in this case is set to fifty seven. In theory, a greater resolution is achieved by making the number large, but in practice the number needs to be limited to ensure a counter within the FPGA 56 does not return to zero.

The resulting time period, T, is then fed via an RS422 channel to a second FPGA 58 which is contained in the controller/processor 60 of the computer processing and control module 36, the arrangement and operation of which will be described below.

The FPGA 58 takes as input the data from the position encoders 28 and is configured to generate the scan area (C,S) using mathematical algorithms. The output from the second FPGA 58 is then fed to the controller/processor 60 of the computer processing and control module 36. This is performed through a DMA engine.

Based on synchronised operation, the computer processing and control module 36 is therefore configured to correlate or correspond the value of T to its scan area. When the coil 26 moves from one scan area (C,S) to the next, the corresponding value of T is transferred to the controller/processor 60.

Still referring to FIG. 5, the computer processing and control module 36 comprises the controller/processor 60, a touch sensitive display 70 comprised of a display part 71 and a tactile interface part 72, a memory 62, and RAM 68. Hardware keys (not shown) may also be provided. The controller/processor is connected to each of the other components in order to control operation thereof.

The memory 62 may be a non-volatile memory such as a read only memory (ROM), a hard disk drive (HDD)_or a solid state drive (SSD). The memory 62 stores, amongst other things, an operating system 64 and software applications 66. The RAM 68 is used by the controller/processor 60 for the temporary storage of data. The operating system 64 and software applications 66 may contain code which, when executed by the controller/processor 60 in conjunction with the RAM 68, controls operation of each of the hardware components of the computer processing and control module 36.

The controller/processor 60 may take any suitable form. For instance it may be a microcontroller, plural microcontrollers, a processor or plural processors.

The display part 71 of the touch sensitive display 70 is for displaying images and text to users of the module 36 and the tactile interface part 72 is for receiving touch inputs from users.

In some embodiments the computer processing and control module 36 may also be associated with external software application not stored on the module. These may be applications stored on a remote server device and may run partly or exclusively on the remote server device. These applications can be termed cloud-hosted applications. The module 36 may be in communication with the remote server device in order to utilise the software application stored there.

The received value of T for a given scan area (C,S), which represents the un-demodulated oscillating signal received for the scan area, is placed into a First In First Out (FIFO) stack and passed to a Direct Memory Access (DMA) engine and channel to ensure that the Operating System (which is MS Windows-based in this instance) processes the correlated scan data in real time.

The resulting scan data is stored on the memory 62 providing, for each coil 26 on the test head 24, the resulting values of T for each scan area (C,S). Each test head 24 therefore results in values which can be presented as a two-dimensional map based on mill roll surface location.

In a following stage, the values of T are applied to an orthogonal differential mask, effectively to remove the base frequency. The post-masked values are passed through a bandpass Finite Impulse Response (FIR) filter and to a subsequent, defect classification, stage. Where the value of T meets a predetermined defect condition, in this case where its value is above a particular value, it is considered indicative of a defect for that scan area. The defect classification stage identifies the type of defect based on the number of adjacent defective areas, whether lengthwise or circumferential. For example:

less than two adjacent defective areas=crack
greater than two adjacent defective areas=bruise.
Other algorithms can be employed.

Figure 6:
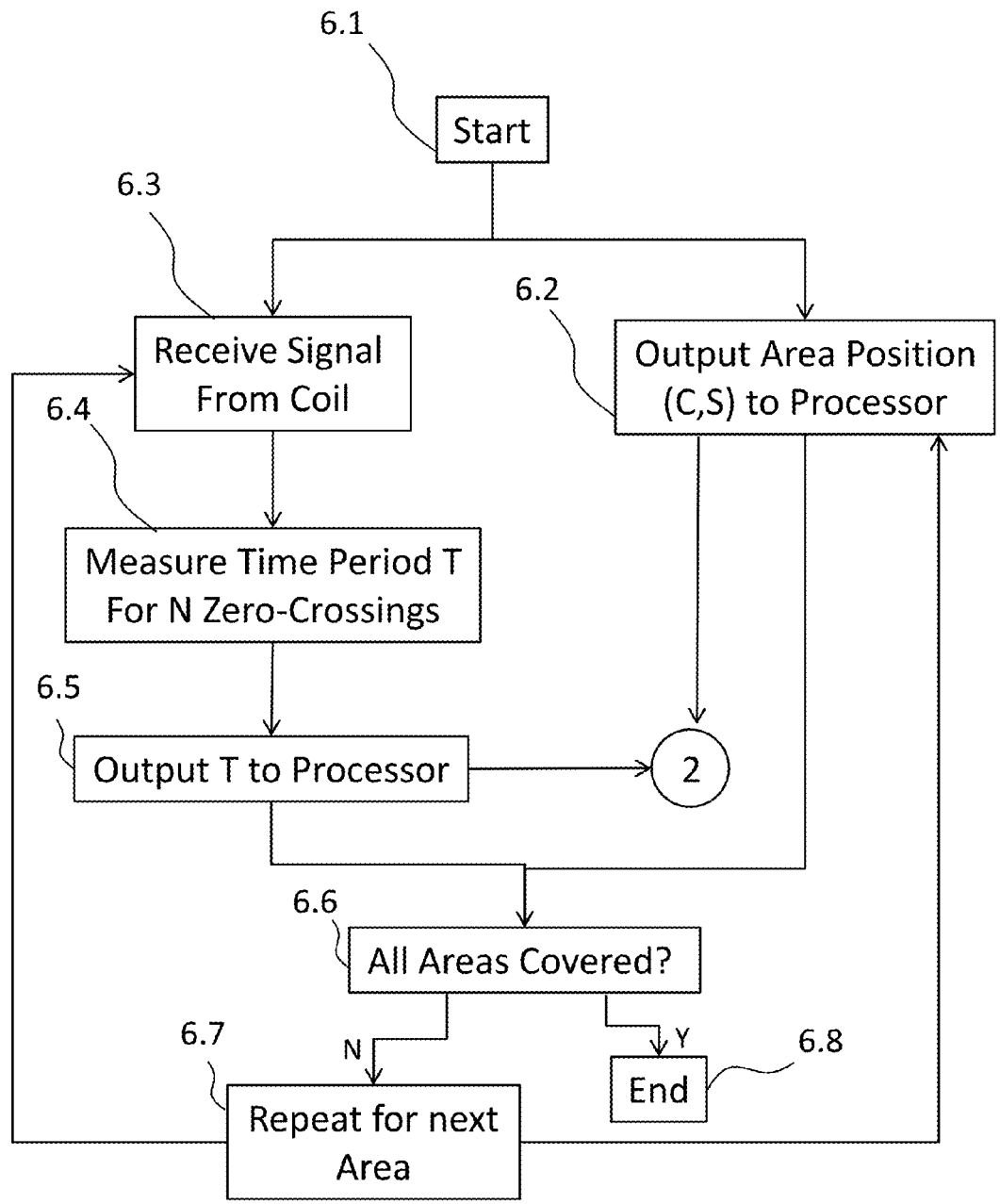
FIGS. 6 and 7 are flow diagrams indicating processing steps performed by the signal processing module and computer processing and control module shown in FIG. 5.

Referring to FIG. 6, the signal processing operations performed by the signal processing module 34 will now be described. Again, for ease of explanation, the steps are described in relation to one coil 26.

A start condition is indicated at step 6.1, which is when the test head 24 begins to move and/or the mill roll begins to rotate to commence the scan process.

In step 6.2 the scan area (C,S) is obtained and output to the controller/processor 60 by the second FPGA 58. In parallel with this step, the signal is received from the coil 26 in step 6.3, the time period T for N zero-crossings is identified in step 6.4 and the value of T is output to the controller/processor 60 in step 6.5.

In step 6.6 the software application 66 determines if all scan areas (C,S) of the mapped roll mill surface have been scanned. If not, the process repeats from steps 6.2 and 6.3 for the subsequent area, and so on until all scan areas have been scanned. When all scan areas have been scanned, the scan process ends in step 6.8.

Figure 7:
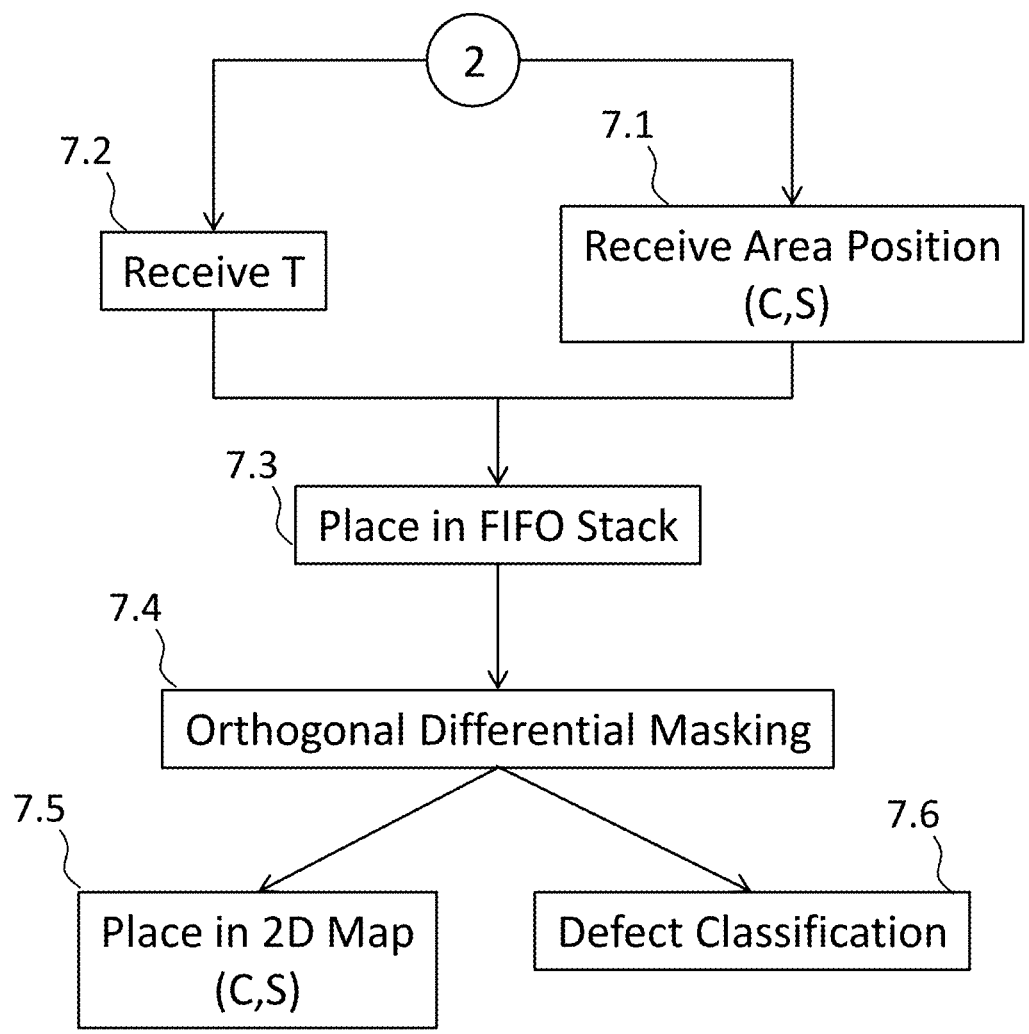

Referring now to FIG. 7, the processing steps performed by a software application 66 when executed on the controller/processor 60 will now be described. Step 7.1 indicates receipt of the scan area (C,S) and step 7.2 indicates receipt of the value of T.

In step 7.3, the corresponding values are placed in the FIFO stack. In step 7.4, orthogonal differential masking is performed. In step 7.5, the resulting masked values of T are stored in the memory 62 as a 2-dimensional map. Step 7.6 indicates the defect classification step, mentioned above.

The software application 66 is further configured to generate a visual representation of the scanned surface, or scan map, following the scan process. A scan map is a two-dimensional representation of the scan areas over the mill roll surface.

Figure 8:
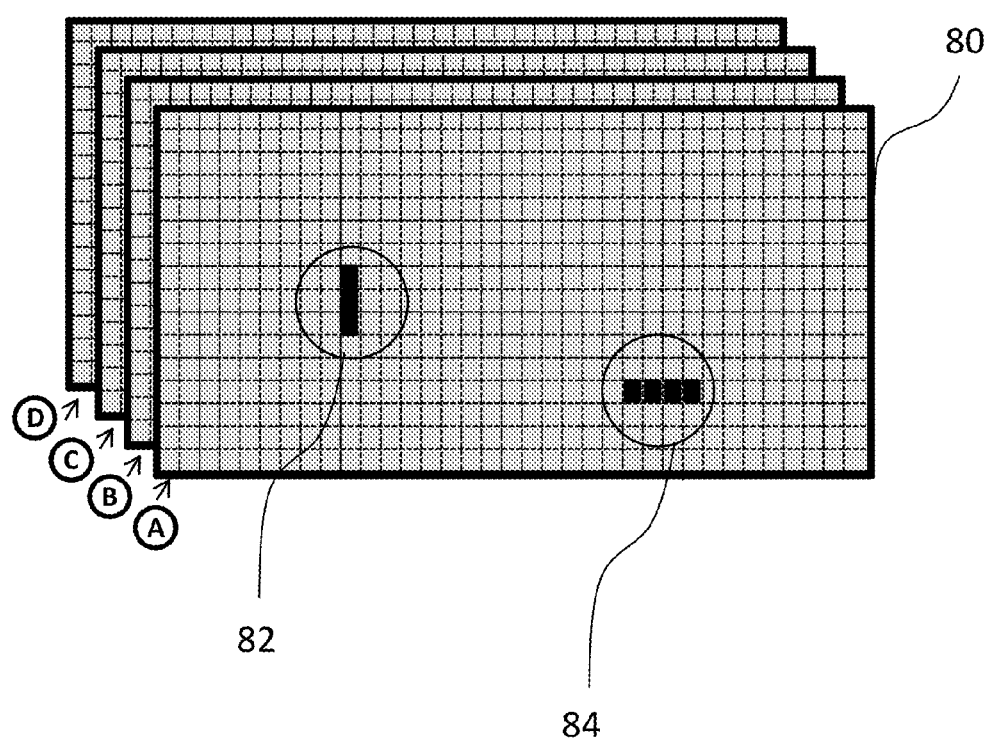
FIG. 8 is view of a user interface of a scan map displayed on a computer display, including a plurality of defective regions.
Figure 9:
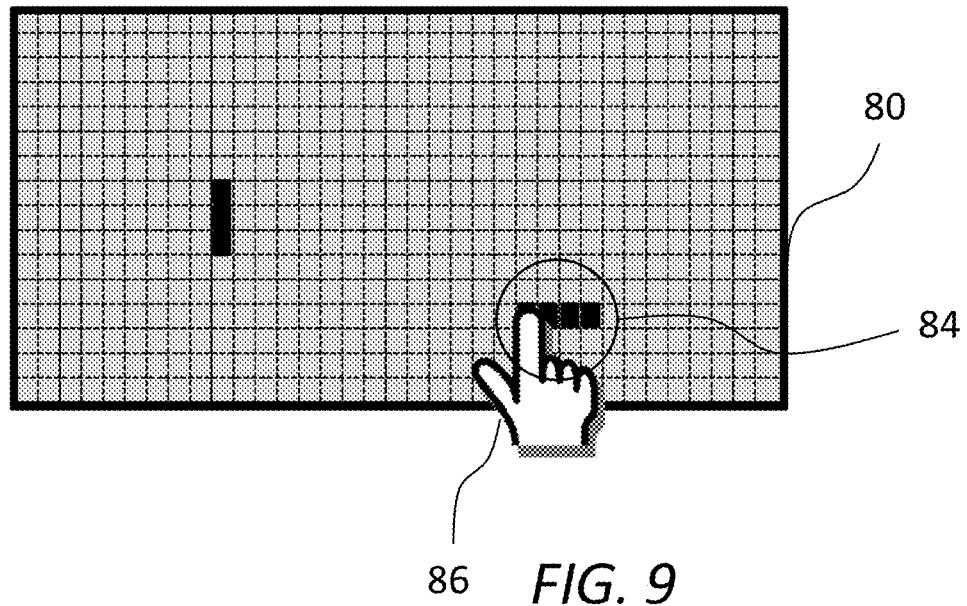
FIG. 9 is a view of the user interface shown in FIG. 8 when displayed using a touch-sensitive display for receiving user selections through the display.

FIG. 8 represents a GUI showing four overlaid scan maps for each of the four coils 26 on the test head 24; these are labelled A, B, C and D. The GUI is output on the touch-sensitive display 70. User selection of the scan map to be displayed on the top level is responsive to user-selection via the tactile interface 72, e.g. by touching the letter label or a menu option presented below the scan map.

The software application generates, for each scan area, a visual indication of defects identified; this may be by way of using different colours or shades of grey relative to the value of T. A low value of T, indicative of no or little change in frequency at the coil 26, is represented by a light grey colour. Defects identified by larger values of T result in a darker colour. In the case of FIG. 8, the uppermost scan map 80 representing coil A indicates two defects 82, 84. A first defect 82 indicates a circumferential defect formed of three adjacent scan areas of dark colour. A second defect 84 indicates a longitudinal defect formed of four adjacent scan areas of dark colour.

The software application 66 is responsive to user inputs received in relation to the top-level scan map. One useful result of this is to control defect identification.

Defect identification, as explained above in relation to the first embodiment, is the process by which the user interface is used to locate specifically the actual defect location on the mill roll. Manual inspection of the defective area can then be performed and, if necessary, subsequent corrective measures (such as grinding) performed.

Figure 10:
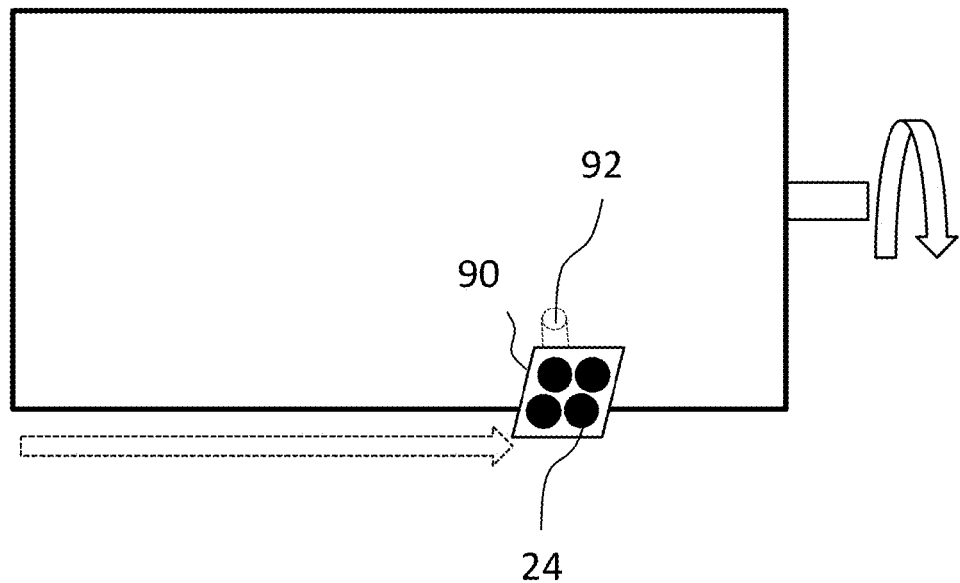
FIG. 10 is a schematic view of the apparatus of FIG. 3 having a test head incorporating a defect indicator, in the form of a light source.

Referring to FIG. 10, the test head 24 has a light source 90, e.g. an LED, mounted thereon which is arranged to direct a focussed beam of light 92 onto the roll mill under the control of the software application 66 when operating in a so-called defect location mode.

In said defect location mode, user inputs received on the tactile interface 72 in relation to a given scan area cause the test head 24 to illuminate the corresponding location on the mill roll surface. More specifically, selecting a scan area causes output of corresponding position data to the position encoders 28, resulting in the system guiding the operator to move the grinder carriage (and hence the test head) to the correct position longitudinally and to rotate the roll to the correct rotational position. Once positioned, the LED 90 on the test head indicates the defect position on the mill roll.

For example, when the test head 24 is located over the position highlighted, the LED 90 located on the test head activates to emit a light over the defect area of the mill roll. The LED may flash on and off as the test head 24 approaches the correct position to further aid the user, the flashing becoming faster as the test head moves towards said correct position. The correct position may be indicated by a non-flashing LED or a change in LED colour.

It will be appreciated that the above described embodiments are purely illustrative and are not limiting on the scope of the invention. Other variations and modifications will be apparent to persons skilled in the art upon reading the present application.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus for detecting defects in a metallic roll mill, comprising:
   a receiver receiving from an eddy coil an oscillating signal induced at the eddy coil as it is moved along a scan path between first and second positions along a longitudinal length of to an underlying metallic surface of the roll mill;
   recording means recording the oscillating signal received along the scan path between the first and second positions;
   output means outputting to a display a representation of the recorded oscillating signal for the scan path; and
   a defect indicator movable along the longitudinal length of the underlying metallic surface and responsive to user selection of part of the signal representation of a circumferential defect to indicate a position on the metallic surface of the metallic roll mill from where the selected part of the signal was received.

2. The apparatus according to claim 1, wherein the recording means is configured to record an oscillating signal received from the eddy coil as it is moved over a plurality of identifiable scan regions or areas of the underlying metallic surface, and wherein the output means is configured to generate and output to a display a two-dimensional map representing the oscillating signal received in relation to each scan region or area.

3. The apparatus according to claim 1, wherein the recording means is configured to record an oscillating signal received from the eddy coil as it is moved between first and second positions for a plurality of generally-parallel scan paths relative to the underlying metallic surface, and wherein the output means is configured to generate and output to a display a two-dimensional map representing the oscillating signal received between the first and second positions for each parallel scan path.

4. The apparatus according to claim 1, further comprising means for identifying, for the scan path, a position of the eddy coil in relation to each of a plurality of adjacent scan areas in-between the first and second positions, and the output means is configured to display an indication of each such scan area and the representation of the oscillating signal received in relation to each scan area.

5. The apparatus according to claim 4, further comprising signal processing means for generating for each scan area a discrete representation of the oscillating signal received in relation to each scan area.

6. The apparatus according to claim 5, wherein the signal processing means is configured to generate the discrete representation of the oscillating signal for a given scan area based on a frequency or number of oscillations received in relation to each scan area.

7. The apparatus according to claim 6, wherein the signal processing means is configured to generate the discrete representation of the oscillating signal for a given scan area by means of measuring the time period required to receive a predetermined number of oscillations for each scan area.

8. The apparatus according to claim 4, wherein the output means is configured to output for each scan area a graphical representation of the oscillating signal representation.

9. The apparatus according to claim 8, wherein the output means is configured to output for each scan area at least one of a shaded graphic with different shades being representative of different characteristics of the oscillating signal representation or a coloured graphic with different colours being representative of different characteristics of the oscillating signal representation.

10. The apparatus according to claim 1, further comprising defect identifying means for identifying automatically from a part of the oscillating signal representation a predetermined characteristic indicative of a defect and indicating the presence of a defect on the display in relation to its position on the underlying metallic surface.

11. The apparatus according to claim 10, further comprising:
   means for identifying, for the scan path, a position of the eddy coil in relation to each of a plurality of adjacent scan areas in-between the first and second positions,
   wherein the output means is configured to display an indication of each such scan area and the representation of the oscillating signal received in relation to each scan area, and wherein the defect identifying means is configured to identify one or more defective scan areas based on identifying the predetermined defect characteristic recorded in relation to one or more scan areas.

12. The apparatus according to claim 11, further comprising:
signal processing means for generating for each scan area a discrete representation of the oscillating signal received in relation to each scan area, wherein the signal processing means is configured to generate the discrete representation of the oscillating signal for a given scan area based on a frequency or number of oscillations received in relation to each scan area, and
wherein the defect identifying means is configured to identify a defective scan area based on the frequency or number of oscillations received meeting a predetermined condition.

13. The apparatus according to claim 11, wherein the defect identifying means is configured automatically to identify a first type of defect by identifying a predetermined number of adjacent defective scan areas along the scan path.

14. The apparatus according to claim 11, wherein the defect identifying means is configured automatically to identify a second type of defect by identifying a predetermined number of adjacent defective scan areas generally orthogonal to the scan path.

15. The apparatus according to claim 1, further comprising means for receiving the user selection through a touch-sensitive display.

16. The apparatus according to claim 15, wherein the defect indicator comprises a light source.

17. The apparatus according to claim 16, wherein the light source is configured to emit a beam of light onto the metallic surface where the selected part of the signal was received from.

18. The apparatus according to claim 1, further comprising a test head on which is mounted one or more eddy coils.

19. The apparatus according to claim 1, wherein the apparatus is configured to detect defects in a substantially cylindrical metal surface.

20. The apparatus of claim 1, wherein:
the recording means records the oscillating signal as a raw oscillation signal as received from the eddy coil;
the output means outputs to the display a representation of the recorded raw oscillating signal for the scan path; and
the defect indicator comprises a light source and is configured to activate and illuminate the circumferential defect on the metallic surface when the defect indictor is located at a corresponding longitudinal position along the length of the metallic roll mill and a corresponding rotational position of the metallic roll mill.

21. A method of detecting defects in a metallic roll mill, the method comprising:
receiving from an eddy coil an oscillating signal induced at the eddy coil as it is moved along a scan path between first and second positions along a longitudinal length of an underlying metallic surface of the metallic roll mill;
recording the oscillating signal received along the scan path between the first and second positions;
outputting to a display a representation of the oscillating signal for the scan path; and
moving a defect indicator along the longitudinal length of the underlying metallic surface and responsive to user selection of part of the signal representation of a circumferential defect to indicate a position on the metallic surface of the metallic roll mill from where the selected part of the signal was received.

22. A non-transitory computer-readable storage medium having stored thereon computer-readable code, which, when executed by computing apparatus, causes the computing apparatus to perform a method comprising:
receiving from an eddy coil an oscillating signal induced at the eddy coil as it is moved along a scan path between first and second positions along a longitudinal length of an underlying metallic surface of a metallic roll mill;
recording the oscillating signal received along the scan path between the first and second positions;
outputting to a display a representation of the oscillating signal for the scan path; and
moving a defect indicator along the longitudinal length of the underlying metallic surface and responsive to user selection of part of the signal representation of a circumferential defect to indicate a position on the metallic surface of the metallic roll mill from where the selected part of the signal was received.

23. A method of detecting and locating defects in a metallic roll mill including the acts of:
passing a test head incorporating an eddy coil circuit along a scan path over a metallic surface of the roll mill, the eddy coil circuit inducing an oscillating signal as it is passed along the scan path between first and second positions along a longitudinal length of the metallic surface of the roll mill;
recording the raw oscillation data received from the oscillating signal along the scan path between the first and second positions for the longitudinal length of the metallic surface under test;
outputting a representation of the raw data on a screen display for the scan path;
displaying a location of the test head on the screen display;
reviewing the screen display to identify potential defects, including circumferential defects; and
moving the metallic surface with respect to the test head or the test head with respect to the metallic surface along the longitudinal length, to a position where the displayed location of the test head and a circumferential defect area identified in the act of reviewing overlap on the screen display.

24. The method according to claim 23, wherein the screen display is a touch screen and wherein the method comprises touching the defect area on the touch screen to effect automated movement of at least one of the test head or metallic surface to the position of overlap.

25. The method according to claim 23, wherein the test head includes a light emitter, which is activated at the point of overlap to emit light on to the metallic surface over the defect area.

* * * * *

UNITED STATES PATENT AND TRADEMARK OFFICE
CERTIFICATE OF CORRECTION

PATENT NO. : 10,073,059 B2
APPLICATION NO. : 14/128386
DATED : September 11, 2018
INVENTOR(S) : Robert Northern Page 1 of 1

It is certified that error appears in the above-identified patent and that said Letters Patent is hereby corrected as shown below:

In the Claims

In Claim 1, Column 9, Line 59, please delete "of to an underlying metallic surface" and insert --of an underlying metallic surface--

Signed and Sealed this
Nineteenth Day of March, 2019

Andrei Iancu
*Director of the United States Patent and Trademark Office*